United States Patent [19]

Siepser

[11] Patent Number: 4,813,954

[45] Date of Patent: Mar. 21, 1989

[54] COMPRESSION, DEFORMATION, DEHYDRATION METHOD OF FABRICATION AND IMPLANTATION OF AN EXPANSILE, HYDROGEL INTRAOCULAR LENS

[76] Inventor: Steven B. Siepser, 866 Dowingtown Pike, West Chester, Pa. 19380

[21] Appl. No.: 107,278

[22] Filed: Oct. 9, 1987

[51] Int. Cl.$^4$ ............................................... A61F 2/16
[52] U.S. Cl. ...................................................... 623/6
[58] Field of Search ........................ 623/6; 351/160 H

[56] References Cited

U.S. PATENT DOCUMENTS 4,556,998 12/1985 Siepser ..................................... 623/6
4,731,079 3/1988 Stoy .......................................... 623/6

Primary Examiner—Ronald L. Frinks
Attorney, Agent, or Firm—Eugene E. Renz, Jr.

[57] ABSTRACT

In the preparation of an expansile, polymeric, hydrogel intraocular lens for small-incision surgery to replace a damaged natural lens, the step of subjecting the polymeric lens material capable of reversible deformation to a compressive force during the drying to cause the disk to deform so that at least one dimension of the lens material decreased, permitting the lens to be inserted in its deformed configuration into the smaller possible wound. An expansile hydrogel intraocular lens material simultaneously reduced in size through dehydration and deformed from its original configuration by compressive forces so that at least one of the dimensions is decreased, said material in its deformed and dehydrated state being stable at room temperature and capable of being stored, shipped, and implanted without refrigeration.

5 Claims, No Drawings

COMPRESSION, DEFORMATION, DEHYDRATION METHOD OF FABRICATION AND IMPLANTATION OF AN EXPANSILE, HYDROGEL INTRAOCULAR LENS

FIELD OF THE INVENTION

This invention relates to an improvement in small-incision cataract surgery. More particularly, it relates to replacing the damaged natural lens of the eye by a substitute implant capable of reversible deformation. This implant comprises an expansile, hydrogel intraocular lens, which has been subjecte dto a compressive force during the drying cycle to casue temporary deformation. This permits insertion of the lens through the smallest possible incision. The invention further relates to novel, compressed, dehydrated intraocular lenses in any of a variety of deformed shapes and to their fabrication.

BACKGROUND OF THE INVENTION

The most common reason for removal of a lens from the eye is the condition od lenticular opacity known as a cataract which occurs primarily in aged people. Previously these patient shad to wear a thick, aphakic over-refraction or a contact lens. This was to compensate for the loss of the human lens which is a major focusing element in the eye. Some people have great difficulty in tolerating the thick glasses. Many have difficulty adjusting to contact lenses and manipulating them. A majority of these patients are unable to tolerate extendedwear contact lenses becaue of dryness in their eyes and the threat of infection.

Today, 95% of the cataract operations performed in the United States involve implanting introocular lenses. Before the introduction of the expansile, hydrogel form of intraocular lenses, the initial insertion in the cornea was large, sometimes more than 7 mm to accommodate the lens and protruding loops. The lens was inserted through the large incision and positioned in the anterior or posterior chamber according to lens design and the needs of the patient. An incision of such size required more post-operative care and caused irritaion, discomfort to the patient, and higher degrees of astigmatism caused by corneal deformation secondary to sutiring. With the advent of expansile, hydrogel intraocular lenses of the type disclosed and claimed in U.S. Pat. No. 4,556,996, the size of the incision was drastically reduced and, therefore, required fewer stuures.

Technology introduced by Staar Surgical of Monrovia, Calif. has already significantly affected cataract surgery. Over 5,000 silicone intraocular lenses have been implanted to date under FDA investigative protocol in the United States. This technology is based on deformation methods as described in U.S. Pat. No. 4,573,998. It does not involve dehydration to maintain deformation.

There is newer technology which is based upon thermo-labile characteristics of hydrogels using low transition temperatures to deform and modify lens configurations for lens implantation. Essentially, these lenses are heated and compressed to smaller shapes and cooled to freeze the material below its transition temperature before it is implanted into the eye where it warms and returns to its original shape and size. This technology, which is distinctly different from the present invention, relies on transition temperatures which allows the compression of an elastic material at a high temperature and reduction of the temperature to "freeze" the material in its deformed state.

The present invention uses the hydrated elasticity to allow deformation under compression during deformation. The material is able to maintain the ideal deformed state due to the rigid nature of the dehydrated hydrogels. This unique concept avoids the need of the injectors or devices for the direct implantation of the materials in the silicone technology. It also avoids the extremely difficult technology of temperature constancy for the thermo-labile products.

Expansile intraocular lenses were designed to take advantage of the swelling and expansion upon hydration of hydrophilic materials. This permitted the lenses prior to implantation to be smaller than other implants or previously non-expansile artificial lenses since the expansile lenses are hydrated by the fluid present in the normal eye and expand to the predetermined desired optically correct size. The intraocular lenses are composed of a dry, solid hydrophilic material capable of expansion by absorbing the fluid pressent in the eye by hydration to a final diameter of from about 5 mm to about 14 mm to reach the predetermined optically correc tlens for the particular patient. These dehydrated lenses have a minimum diameter of about 2 mm and a maximum diameter of about 5 mm in the dry state which, of course, is less than the diameter of existing lenses. This permitted the implantation of intraocular lenses through an incision corresponding to less than 5 mm diameter compared to the non-expansile intraocular lenses which required an incision of at least 7 mm and up to 10 mm.

The need for still smaller intraocular lenses for use primarily in cataract surgery has been recognized recently. While gains in minimizing the trauma of cataract surgery to the elderly patients who are the primary victims of cataracts have been substantial as the result of using expansile hydrogel intraocular lenses and newer lens technology, some of these gains have been negated by the relatively large size of the lenses which still require relatively large incisions, insertion devices and tecyhnologically difficult maneuvering. All operations, of course, require an incision into the eye. The incision must, of course, be large enough to remove the old lens, preferably by phacoemulsification, and insert the new, yet kept as small as possible to minimize trauma to the patient.

It is an object of this invention to fabricate an intraocular lens that can be inserted through a very small phacoemulsification wound and yet provide all the optical qualities of larger lenses now in use.

It is another object to fabricate expansile, hydrogel intraocular lenses capable of returning to their original sizes after compressive deformation and dehydration which will allow insertion through small, phaceomulsification wounds.

Still another object of the invention is to provide an improved expansile, hydrogel intraocular lens which is deformed prior to the time of implantation by compressive forces so that it can pass in its deformed configuration through very tiny incisions.

Still another object of the invention is to reduce trauma and post-operative astigmatism and to decrease the physical and visual rehabilitation time following small incision cataract surgery.

SUMMARY OF THE INVENTION

The foregoing and other objects of the invention, which will become apparent below, are achieved by subjecting an expansile, hydrogel intraocular lens during its dehydration phase to a compressive force applied to the lens so as to cause the lens to change from its round or disk shape to a form in which at least one dimension is smaller than the others permitting insertion through the smallest incision possible. For example, one can place a 5.8 lens through a 3.5 mm incision using dehydration shrinkage alone. With the use of the compression deformation process, the same lens can pass through a 3 mm incision or less due to the elongation and decrease in cross-sectional dimensions as a result of the compression process. In this manner, the effective cross-sectional diameter of the equator is reduced and allows use of a smaller incision. The reduction in cross-sectional diameter at the equator allows insertion through incisions approximately 1-3 mm smaller in width then would ordinarily be required for a lens subjected to dehydration only. Any of a variety of deformed shaped including rolling or folding are possible although the oval shape is preferred.

The material from which the expansile, intraocular lens is made possesses sufficient memory to return to its original configuration upon rehydration. Thus, as the lens rehydrates intraocularly, the natural flexibility and memory of the material returns and the lens resumes its original configuration. After intracameral placement, the intraocular lens returns to tis original shape. Thus, a dehydrated compressed lens takes advantage of small incision surgery making the operation less traumatic for the eye and reducing post operative astigmatism.

DETAILED DESCRIPTION OF THE PREFERRED EMBODIMENT

Preferred emboidment procedure for implantation of the expansile intraocular lens in its hardened, compressed, dehydrated, i.e. xerogel, state is as follows: The initial incision is made in the cornea of about 1-3 mm, which is smaller than is possible for insertion when the intraocular lens has not been deformed. A small phacoemulsification needle is inserted through the incision to phacoemulsify the cataractous lens and remove it by suction leaving the lens casule intact. The hard, deformed, dehydrated intraocular lens is then inserted through the small incision utilizing its deformed shape and implanted in the lens chamber. At this point, the intraocular lens is bathed by the aqueous humor which fills the anterior chamber of the eyeball. The hydrophilic material returns to its original shape, i.e. the shape or configuration it had prior to comression, and expands to apprxoimately 180% of its original diameter. If, for example, the lens in its dry state is 4 mm in diameter, and has a water content of 180%, it will swell or expand to about 7 mm. The lens will swell to its soft, hydrated form in about 1 to 2 hours or so. The lens rehydrates, expands and returns to its original shape and to a size which is larger than the incision site and which provides an optically correct fit, whereupon spherical and edge aberrations are avoided. The small incision is the sutured.

It is to be understood that any of the presently available hydrogel intraocular lenses can be used in the process of this invention whereby the material is compressed and deformed during the drying phase. Particularly preferred lenses for use in this invention are those described and claimed in U.S. Pat. No. 4,556,998 and in my copending application, Ser. No. 07/107,281, HIGH REFRACTIVE INDEX POLYMERIC COMPOSITIONS SUITABLE FOR USE AS EXPANSILE HYDROGEL INTRAOCULAR LENSES, filed concurrently herewith.

In order to better understand the benefits accrued from the present invention, the preferred embodiment is described within the framework of the entire procedure from lesn fabrication and preparation to implantation methodology. This embodiment involves lathe cutting, machining and polishing. Of course, antoher method involving castin or injection molding could be used. As intraocular lens is fabricated in a conventional manner from a polymeric hydrogel material to the exact diameter required to replace the removed natural lens in the lens chamber.

The lens is immersed in an aqueous bath and then subjected to the dual simultaneous process of dehydration (to reduce its overall size) and compression to temporarily deform, roll or fold the lens such that at least one dimension is smaller than the others. The dehydration process wherein an intraocular lens fabricated of any presently available polymeric hydrogel material can be reduced in size by removing up to 80% of the water resident in the material is well known in the art. To condition the lens such that it can be inserted through a smaller corneal incision than that which would be required for a lens subjected to dehydration only, compressive force is applied to temporarily cause deformation or elongation during dehydration. When the lens reaches its xerogel state, it maintains the deformed shape until rehydration. This allows introduction of the deformed dry lens through a small incision. For exmaple, an intraocular lens initially fabricated in a circular or disk configuration is subjected to a compressive force across its diameter and temporarily deformed into an egg-shaped or elliptical configuration wherein the minro axis is temporarily smaller than the original dehydrated lens disk diameter and the major axis temporarily larger. As a consequence, the intraocular lens can now be implanted through a smaller incision wound by inserting the major axis of the elliptically deformed lens through the incision. Since polymeric hydrogel materials may possess different elasticity properties, care must be exercised in the application of the compressive force such that permanent deformation is precluded. Generally, polymeric hydrogel materials retain sufficient restorative memory to withstand up to about 50% compressive deformation.

After implantation, the intraocular lens immediately begins to rehydrate and the normal elasticity of the hydrated material returns. The elastic memory of the polymeric hydrogel material in its hydrated state returns the lens to its original shape. The aqueous humor which fills the anterior chamber of the eyeball is absorbed by the hydrophilic material expanding the lens to approximately 180% of its original diameter. If, for example, the lens in its dry state is 3.2 mm in diameter and has a water content of 67% it will swell or expand to about 5.8 mm. The lens expands to a size larger than the incision site and will swell to its soft, hydrated state necessary to provide an optically correct size to avoid spherical and edge aberrations.

One of the advantages of the present invention is that it allows the shipping and storage of intraocular lenses in their deformed state without refrigeration. Since the deformed state is maintained in dehydration, the surgeon can introduce the lens without any specially designed instruments or technically demanding maneuvers. Since the intraocular materials utilized in the present invention maintain their shape in nromal temperature ranges without refrigeration, the deformed lenses, including the folded and rolled forms, need no intraoperative idevices as their shapes are maintained by dehydration alone. The deformation is reversed when the elastic memory of the hydrogel returns upon rehydration.

What is claimed is:

1. In the process of preparing an expansile hydrogel intraocular lens having a predetermined water level content and a predetermined shape for small incision implantation to replace a damaged natural lens in an otherwise functional eye of a patient, the concurrent steps of subjecting th lens to deformation by a compressive force and dehydration to a water level less than the said predetermined level so as to have at least one dimension of the lens decreased, whereupon the lens will hold its deformed shape and reduced size during storage, shipment, and implantation irrespective of temperature and upon rehydration with body fluids present in the eye, the lens will return to its predetermined shape and swell to its desired size.

2. A dehydrated, deformed expansile hydrogel intraocular lens prepared as set forth in claim 1.

3. An expansile hydrogel intraocular lens material simultaneously reduced in size through dehydration and deformed from its original configuration by compressive forces so that at least one dimensions of the lens material is decreased, said lens material being characterized by returning to its original shape upon rehydration with body fluids following implantation in the eye and swelling to its desired size, said lens material in its deformed and dehydrated state being stable at room temperature and capable of being stored, shipped and implanted without refrigeration.

4. The lens material of claim 3 in the form of an oval.

5. The lens material of claim 3 having a diameter no greater than 3.2 mm.

* * * * *